(12) United States Patent
Divisi

(10) Patent No.: US 10,465,846 B2
(45) Date of Patent: Nov. 5, 2019

(54) MONITORING DEVICE AND METHOD OF AN OIL FLOW MIXED WITH AIR

(71) Applicant: DROPSA S.p.A., Milan (IT)

(72) Inventor: Walter Divisi, Monaco (MC)

(73) Assignee: DROPSA S.P.A., Milan (IT)

( * ) Notice: Subject to any disclaimer, the term of this patent is extended or adjusted under 35 U.S.C. 154(b) by 189 days.

(21) Appl. No.: 15/649,723

(22) Filed: Jul. 14, 2017

(65) Prior Publication Data

US 2018/0017211 A1    Jan. 18, 2018

(30) Foreign Application Priority Data

Jul. 18, 2016    (IT) .................. 102016000075023

(51) Int. Cl.
| | | |
|---|---|---|
| *F16N 29/02* | (2006.01) | |
| *F16N 7/30* | (2006.01) | |
| *G01N 33/28* | (2006.01) | |
| *F16N 7/32* | (2006.01) | |
| *G01P 13/00* | (2006.01) | |
| *G01N 33/30* | (2006.01) | |
| *F16N 7/00* | (2006.01) | |
| *F16N 29/00* | (2006.01) | |
| *G01F 1/74* | (2006.01) | |

(52) U.S. Cl.
CPC .............. *F16N 29/02* (2013.01); *F16N 7/30* (2013.01); *F16N 7/32* (2013.01); *G01N 33/28* (2013.01); *G01N 33/2894* (2013.01); *G01N 33/30* (2013.01); *G01P 13/0086* (2013.01); *F16N 7/00* (2013.01); *F16N 29/00* (2013.01); *F16N 2250/34* (2013.01); *G01F 1/74* (2013.01)

(58) Field of Classification Search
CPC ... F16N 29/02; F16N 7/30; F16N 7/32; F16N 29/00; F16N 7/00; F16N 2250/34; G01N 33/28; G01N 33/2894; G01N 33/30; G01P 13/0086; G01F 1/74
USPC ......................................................... 250/253
See application file for complete search history.

(56) References Cited

U.S. PATENT DOCUMENTS

| | | |
|---|---|---|
| 3,308,300 A | 3/1967 | Kadivnik |
| 2006/0261295 A1* | 11/2006 | Barea ...................... F16N 29/02 |
| | | 250/573 |

FOREIGN PATENT DOCUMENTS

| | | |
|---|---|---|
| JP | H02271197 A | 11/1990 |
| JP | 2011149706 A | 8/2011 |
| WO | 2004079254 A1 | 9/2004 |

OTHER PUBLICATIONS

Search Report and Written Opinion dated Jun. 6, 2017 for Italian patent application No. 201600075023.

* cited by examiner

*Primary Examiner* — David P Porta
*Assistant Examiner* — Meenakshi S Sahu
(74) *Attorney, Agent, or Firm* — Vorys, Sater, Seymour and Pease LLP

(57) ABSTRACT

A monitoring device of an oil flow mixed with air, including a tubular element coupled with at least one first and one second photoelectric sensor that emit a radiation along a first and a second optical line respectively, the tubular element being at least partially transparent to the radiation, the first and the second photoelectric sensor being mounted on the tubular element so that the first and the second optical line are mutually angled.

17 Claims, 3 Drawing Sheets

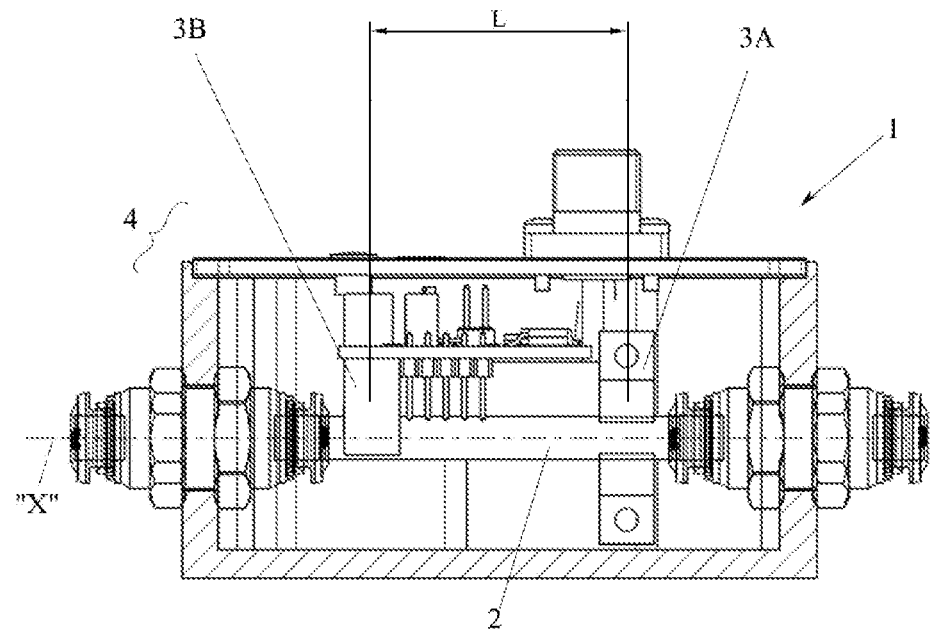
FIG.2
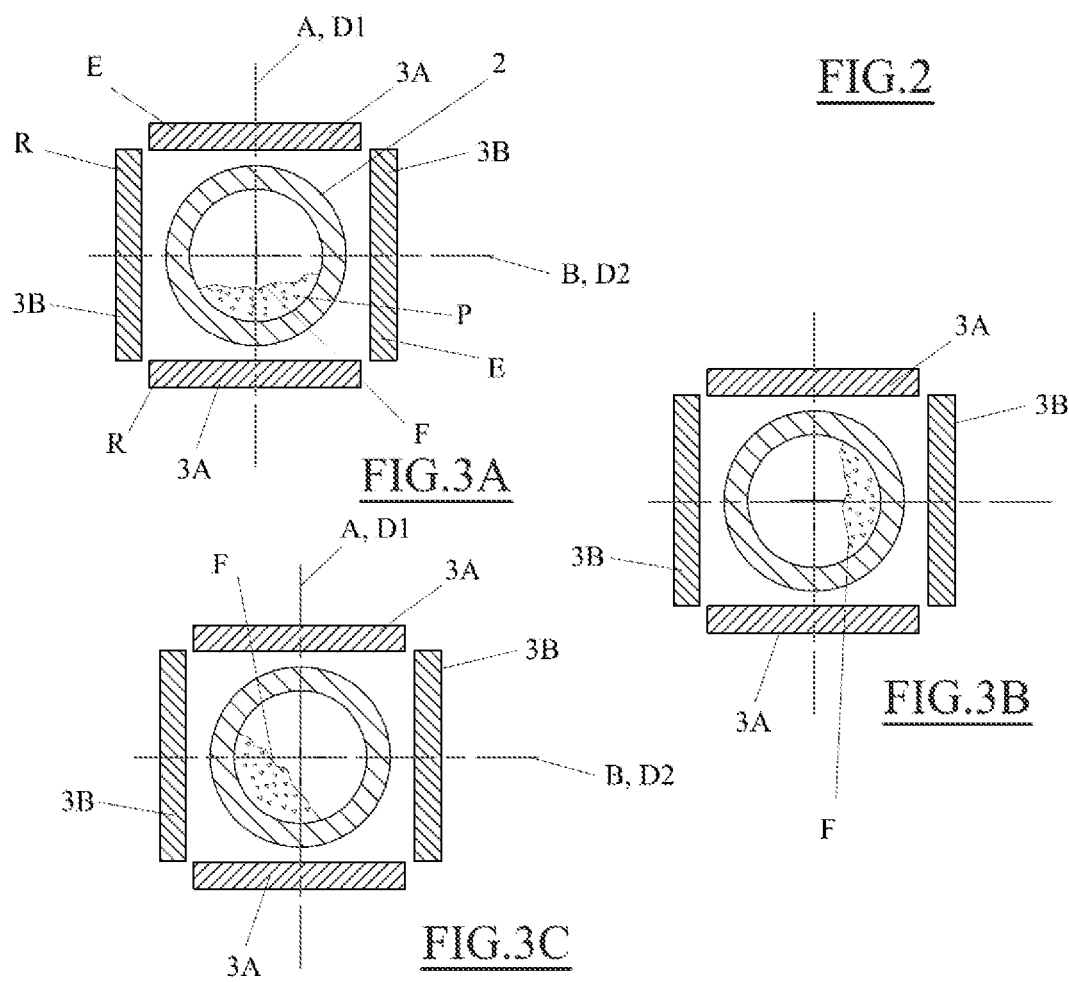
FIG.3A
FIG.3B
FIG.3C

MONITORING DEVICE AND METHOD OF AN OIL FLOW MIXED WITH AIR

This claims the benefit of Italian patent application no. 102016000075023, filed Jul. 18, 2016, incorporated herein by reference.

FIELD OF THE INVENTION

The present invention relates to device and to a method to monitor an oil flow mixed with air.

In particular, it relates to a photoelectric sensor oil monitoring device.

PRIOR ART

As is known in air/oil lubrication systems, a flow of pressurised oil is mixed with a flow of compressed air. The flow of air mixed with oil is conveyed on a mechanical component, thus obtaining a combined effect of lowering the temperature of the component and a particularly effective lubrication.

Although the components of the current lubrication systems are extremely reliable, in some critical situations it is necessary to monitor "in line" the oil flow mixed with air delivered by the lubrication system because, especially when the oil flow rates are very small (minimal lubrication), malfunctions may happen.

To this end, monitoring devices of the oil flow have been designed that through a photoelectric sensor, may detect the oil flow inside a conduit.

These devices work quite well in the presence of a continuous oil flow, without air, but they are hardly adaptable to air/oil systems.

In particular, if the oil flow rates are very low, as is the case in the context of minimal lubrication, the performance of known devices is not acceptable.

SUMMARY OF THE INVENTION

The object of the present invention is to provide an oil monitoring device and method to monitor an oil flow mixed with air which overcomes the technical drawbacks of the prior art.

A further object of the present invention is to provide a monitoring device and a method that is able to accurately detect an oil flow in an air/oil lubrication line.

These and other objects are achieved by a device and a method implemented according to the technical teachings of the appended claims.

BRIEF DESCRIPTION OF THE FIGURES

Further features and advantages of the invention will become apparent from the description of a preferred but non-exclusive embodiment of the device, shown by way of a non-limiting example in the accompanying drawings, in which:

FIG. 2 shows a simplified sectional view of the device in FIG. 1 when assembled;

FIGS. 3A-3C show schematic views illustrating the operating principle of the device in FIG. 1;

DETAILED DESCRIPTION OF THE INVENTION

Figure 1:
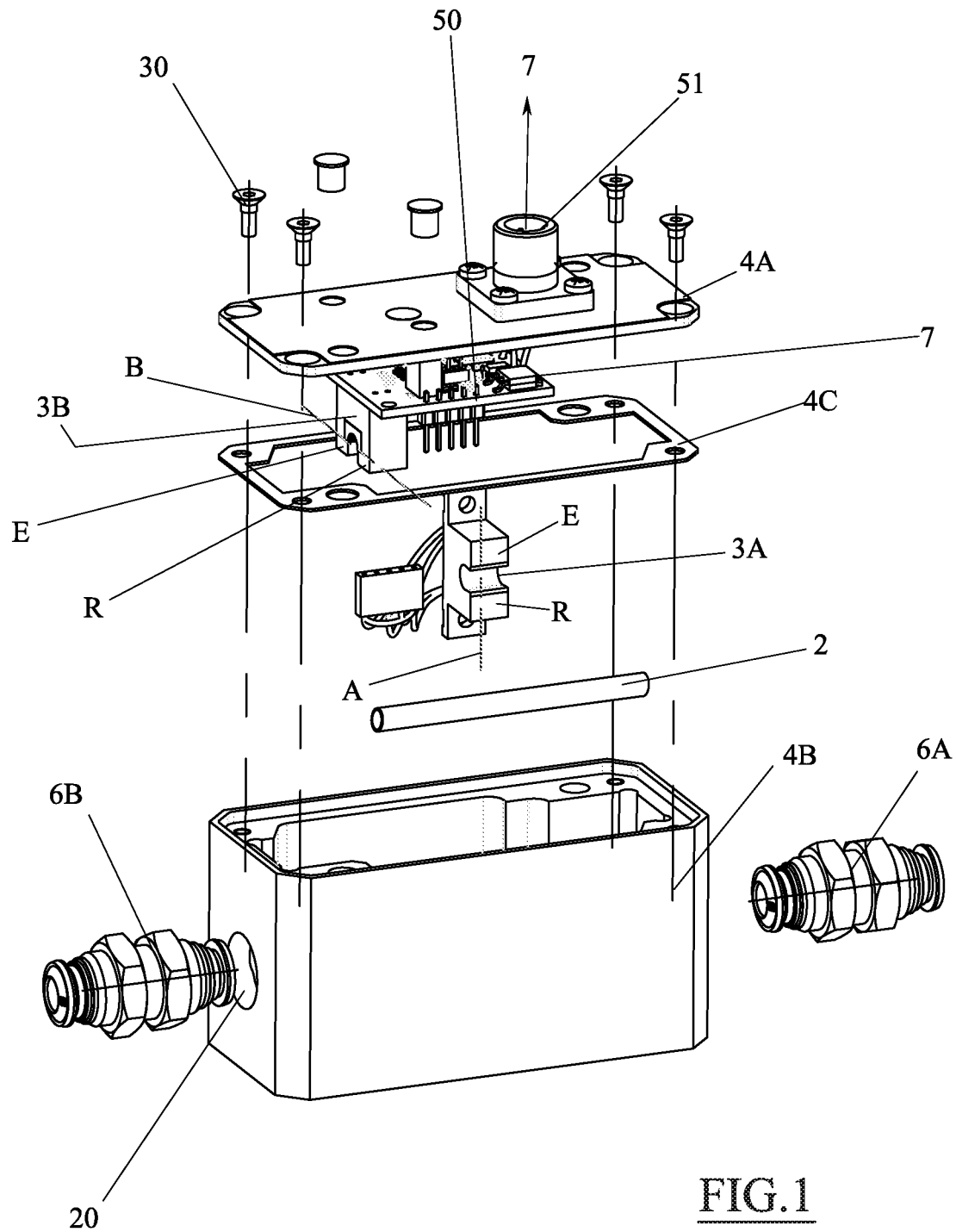
FIG. 1 shows a simplified exploded perspective view of a device according to the present invention.

With reference to the above figures, an oil monitoring device, suitable to monitor an oil flow mixed with air, is shown, indicated as a whole with reference numeral 1. The oil flow, it is in particular a minimal oil flow. In this text, by minimal oil flow it is meant a very low flow, ranging from 10 mm cubes per minute to 100 mm cubes per minute, but preferably between 30 and 40 mm cubes per minute (one drop per minute).

The device comprises a housing 4 or frame, supporting a plurality of elements arranged therein. Specifically, housing 4 has a hollow body 4B and a cover 4A attached to the hollow body 4B with appropriate screws or other suitable means. A seal 4C may be interposed between the hollow body 4B and cover 4A.

As can be seen in FIG. 1, the hollow body has two through holes 20 where a pair of couplings 6A, 6B are fastened, advantageously of the automatic type, and configured to be coupled with a traditional air/oil lubrication line.

Between the two couplings, inside the hollow body 4B, a tubular element 2 is provided. FIG. 2 shows a simplified sectional view of the oil monitoring device 1 in FIG. 1 when assembled. This also shows tubular element 2 and its longitudinal axis X. FIG. 2 showing a longitudinal sectional view. FIGS. 3A, 3B, and 3C show transverse cross-sectional views illustrating the operating principle of the device 1 in FIG. 1 and indicate a first optical line A and the longitudinal axis X of the tubular element 2 will lie on a first phantom plane and the second optical line B and the longitudinal axis X of the tubular element 2 will lie on a second phantom plane. FIGS. 3A, 3B, and 3C also show the first optical line A is aligned to a first diameter D1 of the tubular element 2 and the second optical line B is aligned to a second diameter D2 of the tubular element 2, wherein the first diameter A and the second diameter B are mutually angled in these transverse cross-sectional views of the tubular element 2. As a result, the first phantom plane on which the first diameter A and the longitudinal axis X lie and the second phantom plane on which the second diameter B and the longitudinal axis X lie are also mutually angled. FIGS. 3A, 3B, and 3C, for example, show the first diameter A and the second diameter B being mutually angled (intersecting) to form a perpendicular angle.

When the couplings are coupled to a lubrication line on which device 1 is installed, an air/oil flow flows through the tubular element 2, which is sealably inserted into the line itself (in series).

Figure 4:
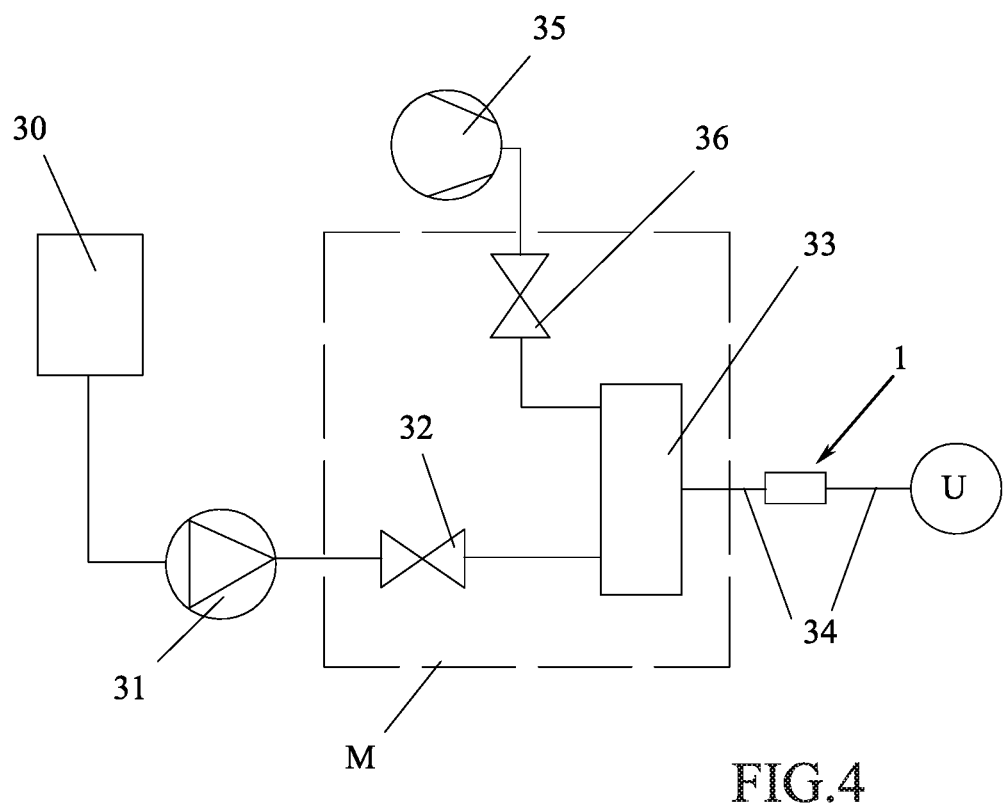
FIG. 4 shows a schematic view of an air oil lubrication system in which the device of the present invention can be installed.

An example of a lubrication system 40 where device 1 can be effectively used is shown in FIG. 4. It may comprise a lubricant tank 30, for example oil, and means for raising the oil pressure 31 (such as a pump).

In some embodiments, tank 30 may be placed under pressure (such as through a pneumatic system), and so the oil can be pressurised already at the outlet of the tank itself.

At least one oil flow regulator 32 is further provided (advantageously with a needle valve) and at least one mixer 33 of the oil with an air flow. The mixer mixes the air and the oil in order to obtain a good distribution of the oily particles in the air flow, directed from conduit 34 towards a utility U (such as a bearing).

In system 40 shown in FIG. 4, the pressurised air is supplied by a compressor 35 (such as of the alternating type with compressed air tank attached), which introduces air under pressure, optionally regulated by a valve 36, into mixer 33.

In some cases, various parts of the system can be integrated into a single modular element M, such as described in the patent document EP2333395 A1, incorporated herein as a reference.

Device 1 may be placed in series to conduit 34, through couplings 6A and 6B, to detect the presence of a flow of air mixed with oil that flows into conduit 34 itself.

Going back to the description of device 1, it is seen that at least a first and a second photoelectric sensor 3A, 3B are coupled to the tubular element 2. The two photoelectric sensors are substantially identical, but are mounted on the tubular element (so as to be able to read an air/oil flow present into the same) in an axially spaced manner (L), and at different angles with respect to the axis of the tubular element.

Specifically, each sensor comprises an emitter E directly (or indirectly) facing towards a receiver R. The emitter may be of the LED type and may emit an infrared radiation with a wavelength of between 0.7 μm and 1 mm, preferably between 0.7 μm and 3 μm (but even more preferably between 0.8 μm and 1 μm). In any case, the emitter must emit a radiation to which the tubular element 2 is at least partially transparent. Advantageously, the tubular element is made of a nearly transparent plastic (such as PA 6, marketed under the tradename Rilsan, by Arkema). These tubular elements are also known as clear tubes. As an example, the tubular element may have an outer diameter of between 1.5 mm and 7 mm.

Receiver R may be a phototransistor.

According to the present invention, the first 3A and the second photoelectric sensor 3B are coupled to the tubular element so that the first and the second optical line A, B of the sensors are mutually angled. The first and the second optical line A, B may be radially angled with respect to the tubular element.

In the present text, the term optical line of the photoelectric sensor (line of sight) means axis A, B of that spatial region where the emitter is directly or indirectly (if it is a reflective sensor) facing the receiver.

FIGS. 3A to 3C schematically show the positioning of the photoelectric sensors 3A, 3B with respect to the tubular element. As can be easily seen, the first optical line A (of the first photoelectric sensor 3A) is aligned with a first diameter D1 of the tubular element while the second optical line B (of the second photoelectric sensor 3B) is aligned with a second diameter D2 of the tubular element. The first and the second diameter D1, D2 being mutually angled by an angle α>0, and advantageously of 90°±5°. Angle α, however, may be between 30°±5° and 90°±5°.

If there are more than two sensors, such as three, angle α may advantageously be 30°±5°.

The sensors may be mounted on the tubular element 2 without interference or with minimal interference, and may be supported directly or indirectly by housing 4.

The arrangement of the sensors on the tubular element 2 is particularly advantageous as it has been verified that the micro-amounts of oil (usually small drops P) pushed by air are arranged in the tubular element 4 along a band F which has a height of about ¼ the diameter of the tubular element 2.

The particle distribution does not have a constant pattern along the tubular element and the latter can also proceed as a spiral along the walls of the tube. The positioning of band F may also depend to a great extent on the spatial orientation of the tubular element (and thus of device 1) or the air velocity and pressure within the latter, and so it is difficult to determine in advance which part of the tube wall is affected by the flow of oil particles.

The particles are distributed in a non-predictable manner especially when the tubular element is installed in a vertical position (which happens often in lubrication systems), this causing, in conventional monitoring devices, many reading errors.

The presence of a double (or triple, etc.) photoelectric sensor allows detecting the oil trail that travels along the tube wall, in any position it is.

FIGS. 3A-3C show some configurations that the flow of oil particles P can take place into the tubular element 2.

When the oil particles pushed by air are distributed in the configuration in FIG. 3A, i.e. at the bottom of the tubular element, the first photoelectric sensor 3A provides an accurate reading of the presence of oil inside the tubular element. The second sensor 3B instead detects a lower or absent oil passage.

In fact, the beam of radiations emitted by emitter E of the first sensor is mitigated by the presence of the oil particles P (which deviates the radiations or absorbs them). Receiver R of the first sensor, therefore, receives a much smaller amount of radiations than those emitted and thus detects a quantity of oil that flows into the tubular element 2. This does not happen for the second sensor, in this configuration.

Only the reading provided by the first sensor 3A is then considered.

When particles P are distributed according to the configuration shown in FIG. 3B, i.e. along one side of the tubular element, the correct reading will be the one provided by the second sensor 3B.

In a situation such as that shown in FIG. 3C, a reading will be obtained from both sensors, and the reading obtained from the sensor that detects a higher oil flow will be considered.

Basically, with the presence of at least two photoelectric sensors arranged as described above, a reading can be obtained that is always well indicative of the flow of oil particles pushed by the air inside the tubular element 2.

Advantageously, therefore, the sensors work in "OR" mode, then the sensor that provides the highest reading is considered while the other one is disregarded.

In the example shown, the photoelectric sensors 3A, 3B are interfaced with a control unit that manage the readings thereof.

The control unit 7 may be directly housed on a printed circuit 50 provided into the housing, or it may be connected to device 1 through a socket with electrical connectors 51.

In any case, the control unit 7 may be configured to:
a) obtain a first parameter indicative of an amount of oil present in the tubular element detected by the first sensor,
b) obtain a second parameter related to the amount of oil present in the tubular element detected by the second sensor,
c) determine the presence or the absence of an air/oil flow in the tubular element based on the first and/or second parameter.

In essence, device 1 works according to a method for detecting the flow of air/oil inside a tubular element 2 comprising the steps of:

obtaining a first parameter indicative of an amount of oil present in the tubular element detected by the first sensor with a first optical line A, obtaining a second parameter related to the amount of oil present in the tubular element detected by the second sensor with a second optical line B angled from the first optical line A radially with respect to the tubular element, determining the presence or the absence of an air/oil flow in the tubular element based on the first and/or second parameter.

The determination of the presence or absence of an oil flow inside the tubular element may be based on the parameter obtained from that sensor which detects the greatest amount of oil flowing in the tubular element.

Specifically, the parameter may be obtained on the basis of a series of readings made on a single sensor in a predefined time.

According to a particularly advantageous embodiment the parameter is obtained based on the sum of the absolute values of the differences of multiple consecutive readings on the same sensor, in a predefined time interval (such as 10 seconds).

In essence, the algorithm provided for the operation of device 1 can alternate the reading on a sensor or the other every 10 seconds. The same detection algorithm can be executed on each of the two sensors, which specifically can provide for:

calculating the sum of the absolute values of the differences of 100 consecutive readings (one every 100 ms, suitably filtered) in 10 seconds if the result is greater than that calculated 10 seconds before on the other sensor, the value is updated with the newly calculated one switch on the other sensor In this way, the resulting value will always be the higher of the two sensors and that value can be compared with the minimum thresholds values set (for example three values), in order to generate an alarm when the value is less than the threshold.

The algorithm described above allows detecting also the case in which the oil changes path along the tubular element. In this case, the path change is detected at most within 10 seconds (that correspond to the predetermined time interval).

According to a different algorithm, it is possible to make a sum of the readings of the two sensors, but in the tests carried out this algorithm was less performing than the previous one, since in practice it seems that the oil always goes on one or the other sensor.

Various embodiments of the invention have been described but others may be conceived using the same innovative concept.

The invention claimed is:

1. An oil flow monitoring device suitable to monitor a minimal oil flow mixed with air, comprising
a tubular element coupled with a first photoelectric sensor and a second photoelectric sensor,
wherein the first photoelectric sensor comprises a first emitter of a radiation and a first receiver, the first emitter directly or indirectly facing the first receiver,
wherein the second photoelectric sensor comprises a second emitter of a radiation and a second receiver, the second emitter directly or indirectly facing the second receiver,
the first and the second photoelectric sensors having a first and a second optical line respectively, the tubular element being at least partially transparent to said radiation,
the first and the second photoelectric sensor being mounted on the tubular element so that the first optical line and the second optical line are radially angled with respect to the tubular element,
wherein the first optical line is aligned to a first diameter of the tubular element and the second optical line is aligned to a second diameter of the tubular element, the first and the second diameter being mutually angled in a transverse cross-sectional view of the tubular element.

2. The oil flow monitoring device according to claim 1, wherein the first optical line and a longitudinal axis of the tubular element lie on a first phantom plane and the second optical line and a longitudinal axis of the tubular element lie on a second phantom plane.

3. The oil flow monitoring device according to claim 1, wherein the first and the second diameter are mutually angled by an angle in the range of 30°±5° to 90°±5°.

4. The oil flow monitoring device according to claim 1, wherein the first and the second diameter are axially spaced on the tubular element.

5. The oil flow monitoring device according to claim 1, wherein the tubular element is arranged in a housing that contains the first and the second photoelectric sensor, the tubular element being provided with an inlet and an outlet associated with connections for the insertion of the tubular element in an air/oil lubrication line, said connections being constrained to the housing.

6. The oil flow monitoring device according to claim 1, wherein the photoelectric sensors are interfaced with a control unit, configured so as to
a) obtain a first parameter indicative of an amount of oil present in the tubular element detected by the first sensor,
b) obtain a second parameter related to the amount of oil present in the tubular element detected by the second sensor,
c) determine the presence or the absence of an air/oil flow in the tubular element based on the first and/or second parameter.

7. A method for detecting the flow of air/oil inside a tubular element comprising the steps of:
providing the tubular element coupled with at least one first and one second photoelectric sensor, each of the first and the second photoelectric sensor comprising one emitter of a radiation and one receiver, the emitter directly or indirectly facing the receiver, wherein the first optical line is aligned to a first diameter of the tubular element and the second optical line is aligned to a second diameter of the tubular element, the first and the second diameter being mutually angled in a sectional view of the tubular element,
obtaining a first parameter indicative of an amount of oil present in the tubular element detected by the first photoelectric sensor with a first optical line,
obtaining a second parameter related to the amount of oil present in the tubular element detected by the second photoelectric sensor with a second optical line radially angled from the first optical line with respect to the tubular element,
determining the presence or the absence of an air/oil flow in the tubular element based on the first and/or second parameter.

8. The method according to claim 7, wherein the determination of the presence or absence of an oil flow inside the tubular element is based on the parameter obtained from that sensor which detects the greatest amount of oil flowing in the tubular element.

9. The method according to claim 7, wherein the parameter is obtained based on a series of readings taken during a predefined time interval.

10. The method according to claim 7, wherein the parameter is obtained based on the sum of the absolute values of the differences of multiple consecutive readings on the same sensor, in a predefined time interval.

11. An air/oil lubrication system comprising an oil tank, means for raising the oil pressure, at least one oil flow regulator, at least one mixer for mixing the oil with a pressurised air flow to obtain an air/oil flow, a conduit adapted to convey the air/oil flow to a user, said conduit comprising an oil flow monitoring device according to claim 1.

12. The oil flow monitoring device according to claim 1, wherein the first and the second diameter are mutually angled by an angle of 90°±5°.

13. An oil flow monitoring device suitable to monitor a minimal oil flow mixed with air, comprising
- a tubular element coupled with a first photoelectric sensor and a second photoelectric sensor,
- wherein the first photoelectric sensor comprises a first emitter of a radiation and a first receiver, the first emitter directly or indirectly facing the first receiver,
- wherein the second photoelectric sensor comprises a second emitter of a radiation and a second receiver, the second emitter directly or indirectly facing the second receiver,
- the first and the second photoelectric sensors having a first and a second optical line respectively, the tubular element being at least partially transparent to said radiation,
- the first and the second photoelectric sensor being mounted on the tubular element so that the first optical line and the second optical line are radially angled with respect to the tubular element,
- wherein the first optical line and a longitudinal axis of the tubular element lie on a first phantom plane and the second optical line and a longitudinal axis of the tubular element lie on a second phantom plane.

14. The oil flow monitoring device according to claim 1, wherein the first and the second phantom plane are mutually angled by an angle in the range of 30°±5° to 90°±5°.

15. The oil flow monitoring device according to claim 1, wherein the first and the second phantom planes are axially spaced on the tubular element.

16. The oil flow monitoring device according to claim 13, wherein the tubular element is arranged in a housing that contains the first and the second photoelectric sensor, the tubular element being provided with an inlet and an outlet associated with connections for the insertion of the tubular element in an air/oil lubrication line, said connections being constrained to the housing.

17. The oil flow monitoring device according to claim 13, wherein the photoelectric sensors are interfaced with a control unit, configured so as to
- d) obtain a first parameter indicative of an amount of oil present in the tubular element detected by the first sensor,
- e) obtain a second parameter related to the amount of oil present in the tubular element detected by the second sensor,
- f) determine the presence or the absence of an air/oil flow in the tubular element based on the first and/or second parameter.

* * * * *